United States Patent
Banas et al.

(10) Patent No.: US 7,122,049 B2
(45) Date of Patent: Oct. 17, 2006

(54) ENDOLUMINAL STENT HAVING MID-STRUT INTERCONNECTING MEMBERS

(75) Inventors: Christopher E. Banas, San Antonio, TX (US); David G. Rosenbaum, Glencoe, IL (US)

(73) Assignee: Advanced Bio Prosthetic Surfaces, Ltd., San Antonio, TX (US)

( * ) Notice: Subject to any disclaimer, the term of this patent is extended or adjusted under 35 U.S.C. 154(b) by 78 days.

(21) Appl. No.: 10/803,392

(22) Filed: Mar. 18, 2004

(65) Prior Publication Data

US 2004/0186554 A1    Sep. 23, 2004

Related U.S. Application Data

(60) Provisional application No. 60/455,783, filed on Mar. 19, 2003.

(51) Int. Cl.
*A61F 2/06* (2006.01)
(52) U.S. Cl. .................. 623/1.15; 623/1.17
(58) Field of Classification Search .............. 623/1.15, 623/1.18, 1.19, 1.2, 1.17
See application file for complete search history.

(56) References Cited

U.S. PATENT DOCUMENTS

| | | | | |
|---|---|---|---|---|
| 4,733,665 A | 3/1988 | Palmaz | ........................ | 128/343 |
| 4,739,762 A | 4/1988 | Palmaz | ........................ | 128/343 |
| 4,776,337 A | 10/1988 | Palmaz | ........................ | 128/343 |
| 5,421,955 A | 6/1995 | Lau et al. | ..................... | 216/48 |
| 5,514,154 A | 5/1996 | Lau et al. | ..................... | 606/195 |
| 5,569,295 A | 10/1996 | Lam | ........................ | 606/198 |
| 5,603,721 A | 2/1997 | Lau et al. | ..................... | 606/195 |
| 5,728,158 A | 3/1998 | Lau et al. | ..................... | 623/12 |
| 5,733,303 A | 3/1998 | Israel et al. | .................. | 606/198 |
| 5,735,893 A | 4/1998 | Lau et al. | ..................... | 623/1 |
| 5,759,192 A | 6/1998 | Saunders | ..................... | 606/194 |
| 5,766,238 A | 6/1998 | Lau et al. | ..................... | 623/1 |
| 5,772,864 A | 6/1998 | Moller et al. | .................. | 205/73 |
| 5,776,161 A * | 7/1998 | Globerman | .................. | 606/194 |
| 5,780,807 A | 7/1998 | Saunders | ............... | 219/121.71 |
| 5,807,404 A | 9/1998 | Richter | ........................ | 623/1 |
| 5,817,126 A | 10/1998 | Imran | ........................ | 606/198 |
| 5,843,120 A | 12/1998 | Israel et al. | ................. | 606/198 |
| 5,843,164 A | 12/1998 | Frantzen et al. | ............... | 623/1 |
| 5,853,419 A | 12/1998 | Imran | ........................ | 606/191 |
| 5,868,782 A | 2/1999 | Frantzen | ..................... | 606/198 |
| 5,876,432 A | 3/1999 | Lau et al. | ..................... | 623/1 |

(Continued)

FOREIGN PATENT DOCUMENTS

EP    1 212 986    6/2006

(Continued)

OTHER PUBLICATIONS

"Experimental studies: Are design differences relevant?" by Campbell Rogers, M.D., CardiacCatheterization Laboratory Brigham and Women's Hospital, pp. 1-21 (Sep. 24, 2002).

*Primary Examiner*—Corrine McDermott
*Assistant Examiner*—Thomas J. Sweet
(74) *Attorney, Agent, or Firm*—David G. Rosenbaum; Paul J. Lee; Rosenbaum & Associates, PC

(57) ABSTRACT

An endoluminal stent composed of a plurality of circumferential expansion elements arrayed to form the circumference of the stent and extending along the longitudinal axis of the stent, and a plurality of interconnecting members that interconnect adjacent pairs of circumferential expansion elements, the interconnecting members joining struts of adjacent pairs of interconnecting members at approximate midpoints of the struts.

10 Claims, 7 Drawing Sheets

U.S. PATENT DOCUMENTS

| | | | |
|---|---|---|---|
| 5,919,225 A | 7/1999 | Lau et al. | 623/1 |
| 5,938,682 A | 8/1999 | Hojeibane et al. | 606/198 |
| 6,015,429 A | 1/2000 | Lau et al. | 623/1 |
| 6,033,433 A | 3/2000 | Ehr et al. | 623/1 |
| 6,042,597 A | 3/2000 | Kveen et al. | 606/198 |
| 6,056,776 A | 5/2000 | Lau et al. | 623/1.16 |
| 6,059,808 A | 5/2000 | Boussignac et al. | 606/191 |
| 6,059,810 A | 5/2000 | Brown et al. | 606/198 |
| 6,063,101 A | 5/2000 | Jacobsen et al. | 606/194 |
| 6,066,167 A | 5/2000 | Lau et al. | 623/1 |
| 6,066,168 A | 5/2000 | Lau et al. | 623/1.16 |
| 6,066,169 A * | 5/2000 | McGuinness | 623/1.16 |
| 6,103,320 A | 8/2000 | Matsumoto et al. | 427/535 |
| 6,120,847 A | 9/2000 | Yang et al. | 427/335 |
| 6,124,523 A | 9/2000 | Banas et al. | 623/11 |
| 6,129,755 A | 10/2000 | Mathis et al. | 623/1.15 |
| 6,270,524 B1 | 8/2001 | Kim | 623/1.15 |
| 6,293,966 B1 | 9/2001 | Frantzen | 623/1.15 |
| 6,309,412 B1 | 10/2001 | Lau et al. | 623/1.11 |
| 6,309,414 B1 | 10/2001 | Rolando et al. | 623/1.15 |
| 6,312,463 B1 | 11/2001 | Rourke et al. | 623/1.39 |
| 6,325,821 B1 | 12/2001 | Gaschino et al. | 623/1.15 |
| 6,325,826 B1 | 12/2001 | Vardi et al. | 623/1.35 |
| 6,331,190 B1 | 12/2001 | Shokoohi et al. | 623/1.22 |
| 6,334,870 B1 | 1/2002 | Ehr et al. | 623/1.16 |
| 6,334,871 B1 | 1/2002 | Dor et al. | 623/1.34 |
| 6,336,938 B1 | 1/2002 | Kavteladze et al. | 623/1.15 |
| 6,355,058 B1 | 3/2002 | Pacetti et al. | 623/1.15 |
| 6,387,123 B1 | 5/2002 | Jacobs et al. | 623/1.34 |
| 6,432,133 B1 | 8/2002 | Lau et al. | 623/1.15 |
| 6,451,049 B1 | 9/2002 | Vallana et al. | 623/1.15 |
| 6,461,380 B1 * | 10/2002 | Cox | 623/1.17 |
| 6,475,236 B1 | 11/2002 | Roubin et al. | 623/1.15 |
| 6,485,508 B1 | 11/2002 | McGuinness | 623/1.15 |
| 6,503,272 B1 | 1/2003 | Duerig et al. | 623/1.24 |
| 6,506,211 B1 | 1/2003 | Skubitz et al. | 623/1.15 |
| 6,540,774 B1 * | 4/2003 | Cox | 623/1.15 |
| 6,605,110 B1 * | 8/2003 | Harrison | 623/1.15 |
| 6,613,079 B1 * | 9/2003 | Wolinsky et al. | 623/1.15 |
| 6,673,106 B1 | 1/2004 | Mitelberg et al. | 623/1.2 |
| 6,689,159 B1 | 2/2004 | Lau et al. | 623/1.16 |
| 6,699,278 B1 | 3/2004 | Fischell et al. | 623/1.15 |
| 6,709,454 B1 | 3/2004 | Cox et al. | 623/1.16 |
| 6,730,116 B1 * | 5/2004 | Wolinsky et al. | 623/1.16 |
| 2001/0037146 A1 | 11/2001 | Lau et al. | 623/1.16 |
| 2001/0037147 A1 | 11/2001 | Lau et al. | 623/1.16 |
| 2001/0047200 A1 | 11/2001 | White et al. | 623/1.15 |
| 2001/0047201 A1 | 11/2001 | Cox et al. | 623/1.16 |
| 2001/0056298 A1 | 12/2001 | Brown et al. | 623/1.16 |
| 2002/0007209 A1 | 1/2002 | Scheerder et al. | 623/1.15 |
| 2002/0016623 A1 | 2/2002 | Kula et al. | 623/1.11 |
| 2002/0042649 A1 | 4/2002 | Schaldach et al. | 623/1.15 |
| 2002/0045935 A1 | 4/2002 | Jang | 623/1.16 |
| 2002/0055770 A1 | 5/2002 | Doran et al. | 623/1.15 |
| 2002/0072793 A1 | 6/2002 | Rolando et al. | 623/1.16 |
| 2002/0123798 A1 * | 9/2002 | Burgermeister | 623/1.17 |
| 2002/0156523 A1 | 10/2002 | Lau et al. | 326/1.13 |
| 2002/0183831 A1 | 12/2002 | Rolando et al. | 623/1.15 |
| 2003/0004567 A1 | 1/2003 | Boyle et al. | 623/1.16 |
| 2003/0083646 A1 | 5/2003 | Sirhan et al. | 604/891.1 |
| 2003/0105515 A1 | 6/2003 | Skubitz et al. | 623/1.15 |
| 2004/0054399 A1 | 3/2004 | Roth | 623/1.16 |

FOREIGN PATENT DOCUMENTS

| | | |
|---|---|---|
| FR | 2 777 771 | 10/1999 |
| WO | 01/49212 | 7/2001 |
| WO | 02/38080 | 5/2002 |

* cited by examiner

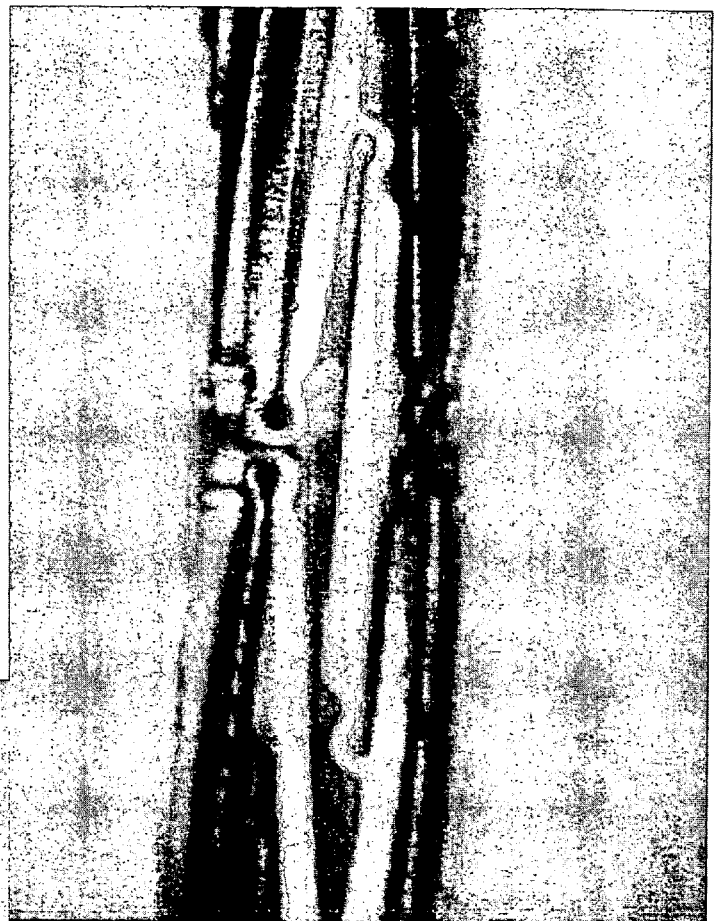
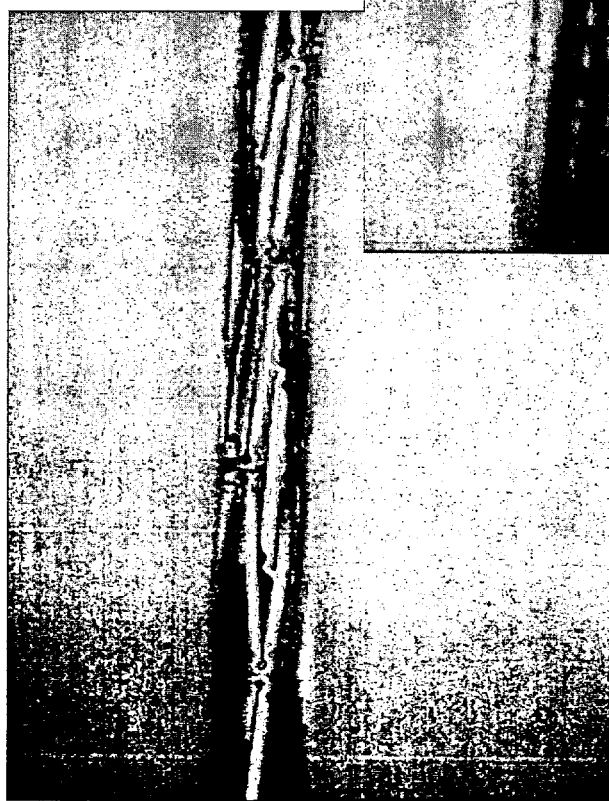
FIG. 7

ENDOLUMINAL STENT HAVING MID-STRUT INTERCONNECTING MEMBERS

CROSS-REFERENCE TO RELATED APPLICATIONS

The present application claims priority to currently pending U.S. Provisional Application Ser. No. 60/455,783 filed Mar. 19, 2003.

BACKGROUND OF THE INVENTION

The present invention relates generally to endoluminal stents, covered stents and stent-grafts designed for delivery into an anatomical passageway using minimally invasive techniques, such as percutaneous intravascular delivery using a delivery catheter passed over a guidewire. More particularly, the present invention relates to endoluminal stents having a scaffold structure and structural geometry which is particularly well-suited for providing physiologically acceptable radial or hoop strength and longitudinal flexibility, while also presenting a luminal surface thereof which presents less obstruction to longitudinal shear forces during fluid flow across the luminal surface of the inventive device while maximizing fatigue life and corrosion resistance. Additionally, the inventive endoluminal stent is characterized by a geometry that uniquely has a negative coefficient of longitudinal foreshortening upon radial expansion. Thus, a unique aspect of the inventive endoluminal stent is that it elongates upon radial expansion.

Endoluminal stents are generally tubular scaffolds fabricated from implantable biocompatible materials. Stents have a generally tubular geometry characterized by a central lumen, a longitudinal axis, a circumferential axis and a radial axis. Conventional endoluminal stents fall within three general classifications: balloon expandable, self-expanding and shape-memory. Balloon expandable stents require mechanical intervention, such as by using a balloon catheter, to apply a positive pressure radially outward from a central lumen of the stent to mechanically deform the stent and urge it to a larger diameter. Self-expanding stents utilize inherent material mechanical properties of the stent material to expand the stent. Typically, self-expanding stents are fabricated of materials that rebound when a positive pressure is exerted against the material. Self-expanding stents are fabricated such that their zero-stress configuration conforms to the second larger diameter. The self-expanding stents are drawn down to the first smaller diameter and constrained within a delivery catheter for endoluminal delivery. Removal of the constraint releases the constraining pressure and the self-expanding stent, under its own mechanical properties, rebounds to the second larger diameter. Finally, shape-memory stents rely upon unique alloys that exhibit shape memory under certain thermal conditions. Conventional shape-memory stents are typically nickel-titanium alloys known generically as nitinol, which have a transition phase at or near normal body temperature, i.e., 37 degrees Centigrade.

The prior art is replete with various stent designs across all stent classifications. One of the difficulties with many conventional stent designs arises due to the conflicting criteria between the desired properties of circumferential or hoop strength of the stent, longitudinal or column strength, longitudinal flexibility, fish-scaling of individual structural members of the stent, fatigue life, corrosion resistance, corrosion fatigue, hemodynamics, radioopacity and biocompatibility and the capability of passing the stent through an already implanted stent. Typically, stents that are designed to optimize for hoop strength typically sacrifice either column strength and/or longitudinal flexibility, while stents that are designed to optimize for column strength often compromise longitudinal flexibility and/or hoop strength.

Most conventional stents exhibit longitudinal foreshortening upon radial expansion of the stent. Longitudinal foreshortening is a well-known property that results from the geometric deformation of the stent's structural members as the stent radially expands from a contracted state to a diametrically expanded state. Several prior art stents have been invented that claim a lack of appreciable foreshortening of the stent as a novel feature of the stent. Heretofore, however, a stent that longitudinally elongates upon radial expansion from a contracted state to a diametrically expanded state is unknown in the art.

It has been found desirable to devise an endoluminal stent which employs a series of first and interconnecting members arrayed in geometrical patterns which achieve a balance between hoop strength, column strength and longitudinal flexibility of the endoluminal stent. Many conventional stents employ a series of circumferential structural elements and longitudinal structural elements of varying configurations. A large number of conventional stents utilize circumferential structural elements configured into a serpentine configuration or a zig-zag configuration. The reason underlying this configuration is the need for radial expansion of the stent. Of these conventional stents which employ serpentine or zig-zag circumferential structural elements, many also employ longitudinal structural elements which join adjacent circumferential structural elements and provide a modicum of longitudinal or column strength while retaining longitudinal flexibility of the device. Additionally, many conventional stents require welds to join mating surfaces of the stent.

Heretofore, however, the art has not devised a unibody stent structural element geometry which achieves a balance between hoop strength, column strength and longitudinal flexibility, degree of longitudinal foreshortening, circumferential strength or hoop strength of the stent, longitudinal strength or column strength, longitudinal flexibility, fish-scaling of individual structural members of the stent, fatigue life, corrosion resistance, corrosion fatigue, hemodynamics, radioopacity, biocompatibility and the capability of passing the stent through an already implanted stent. The term "fish-scaling" is used in the art and herein to describe a condition where some stent structural elements extend beyond the circumferential plane of the stent during either radial expansion, implantation or while passing the stent through a bend in the vasculature. Those of ordinary skill in the art understand that fish-scaling of stent structural elements may cause the stent to impinge or snag upon the anatomical tissue either during endoluminal delivery or after implantation. The term "unibody" as used herein is intended to mean a stent that is fabricated without the use of welds and as an integral body of material.

The inventive endoluminal stent may be, but is not necessarily, fabricated by vapor deposition techniques. Vapor deposition fabrication of the inventive stents offers many advantages, including, without limitation, the ability to fabricate stents of complex geometries, the ability to control fatigue life, corrosion resistance, corrosion fatigue, bulk and surface material properties, and the ability to vary the transverse profiles, Z-axis thickness and X-Y-axis surface area of the stent's structural elements in manners that affect the longitudinal flexibility, hoop strength of the stent and radial expansion profiles.

SUMMARY OF THE INVENTION

Endoluminal stent, covered stent and stent-graft design inherently attempts to optimize the functional aspects of radial expandability, i.e., the ratio of delivery diameter to expanded diameter, hoop strength, longitudinal flexibility, longitudinal foreshortening characteristics, column strength, fish-scaling of individual structural members of the stent, fatigue life, corrosion resistance, corrosion fatigue, hemodynamics, biocompatibility and the capability of stent-through-stent delivery. Conventional stent designs have had to compromise one or more functional features of a stent in order to maximize a particular functionality, e.g., longitudinal flexibility is minimized in order to achieve desirable column strength or high hoop strengths are achieved at the expense of small ratios of radial expandability. It is an objective of the present invention to provide designs for endoluminal unibody stents that achieve balances between the ratio of radial expandability, hoop strength, longitudinal flexibility and column strength, with biocompatibility, hemodynamics, radioopacity, minimal or no fish-scaling and increased capacity for endothelialization.

In accordance with a preferred embodiment of the present invention, the inventive endoluminal stent is formed of a single piece of biocompatible metal or pseudometal and having a plurality of circumferential expansion members co-axially aligned along a longitudinal axis of the stent and a plurality of interconnecting members interconnecting adjacent pairs of circumferential expansion members. Each of the plurality of circumferential expansion members comprises a generally sinusoidal ring structure having successive peaks and valleys interconnected by stent strut members. Each of the interconnecting members interconnects adjacent pairs of circumferential expansion members at approximate mid-points of stent strut members on the adjacent pairs of circumferential expansion members. In order to enhance longitudinal flexibility of the inventive stent, it has been found desirable to include minor terminal regions of each interconnecting member that are narrower in width than a major intermediate region of the interconnecting member. The minor terminal regions are positioned at both the proximal and distal end of each interconnecting member and are narrower in width to enhance flexion at the junction region between the stent strut member and the interconnecting member. Additionally, it has been found desirable to form each of the minor terminal regions of the interconnecting members in the form of generally C-shaped sections extending proximally or distally from the intermediate region of each interconnecting member.

In accordance with all embodiments of the present invention, each of the plurality of circumferential expansion members and the plurality of interconnecting members may be fabricated of like biocompatible materials, preferably, biocompatible metals or metal alloys. In this manner, both the plurality of circumferential expansion elements and the plurality of interconnecting members have like physical material properties, e.g., tensile strength, modulus of elasticity, plastic deformability, spring bias, shape memory or super-elastic properties. Alternatively, the plurality of circumferential expansion members and interconnecting members may be fabricated of biocompatible materials, preferably, biocompatible metals or metal alloys which exhibit different physical or material properties. In this latter case, the plurality of circumferential expansion elements may, for example, be fabricated of a plastically deformable material, such as stainless steel, while the plurality of interconnecting members are fabricated of a shape memory or super-elastic material, such as nickel-titanium alloys, or of a spring biased material, such as stainless steel.

Heretofore, joints between discrete sections of endoluminal stents required welds in order to join sections of the stent. One particular advantage of the present invention is that by forming the stent using vapor deposition techniques, not only are discrete sections atomically joined without the use of welds, but different materials may be employed in different and discrete sections of the stent in order to impart distinct material properties and, therefore, functionality, to the discrete sections.

Finally, the present invention also includes a self-supporting endoluminal graft. As used herein the term "graft" is intended to indicate any type of tubular member that exhibits integral columnar and circumferential strength and which has openings that pass through the thickness of the tubular member. The inventive self-supporting endoluminal graft preferably consists of a member formed of at least one of a plurality of layers, each layer being comprised of a plurality of first and interconnecting members which intersect one another, as described above, to define a plurality of open regions between intersecting pairs of the first and interconnecting members. A web region subtends at least a portion of the open region to at least partially enclose each of the plurality of open regions. Successive adjacent layers of the plurality of layers are positioned such that the open regions are staggered in the Z-axis transverse through the wall of the self-supporting endoluminal graft. By staggering the open regions, interlamellar spaces are created to facilitate endothelialization of the endoluminal graft.

BRIEF DESCRIPTION OF THE FIGURES

FIG. 2 is a plan view of a first embodiment of the inventive endoluminal stent.

FIG. 5 is a plan view of a fourth embodiment of the inventive endoluminal stent.

FIG. 7 is a photomicrograph depicting the inventive endoluminal stent in its constricted diameter for endoluminal delivery within a constraining sheath.

FIG. 8 is a photomicrograph depicting the inventive endoluminal stent partially released from a constraining sheath and radially expanding.

FIG. 9 is photomicrograph depicting the inventive endoluminal stent in its radially enlarged diameter.

DETAILED DESCRIPTION OF THE PREFERRED EMBODIMENTS

Figure 1:
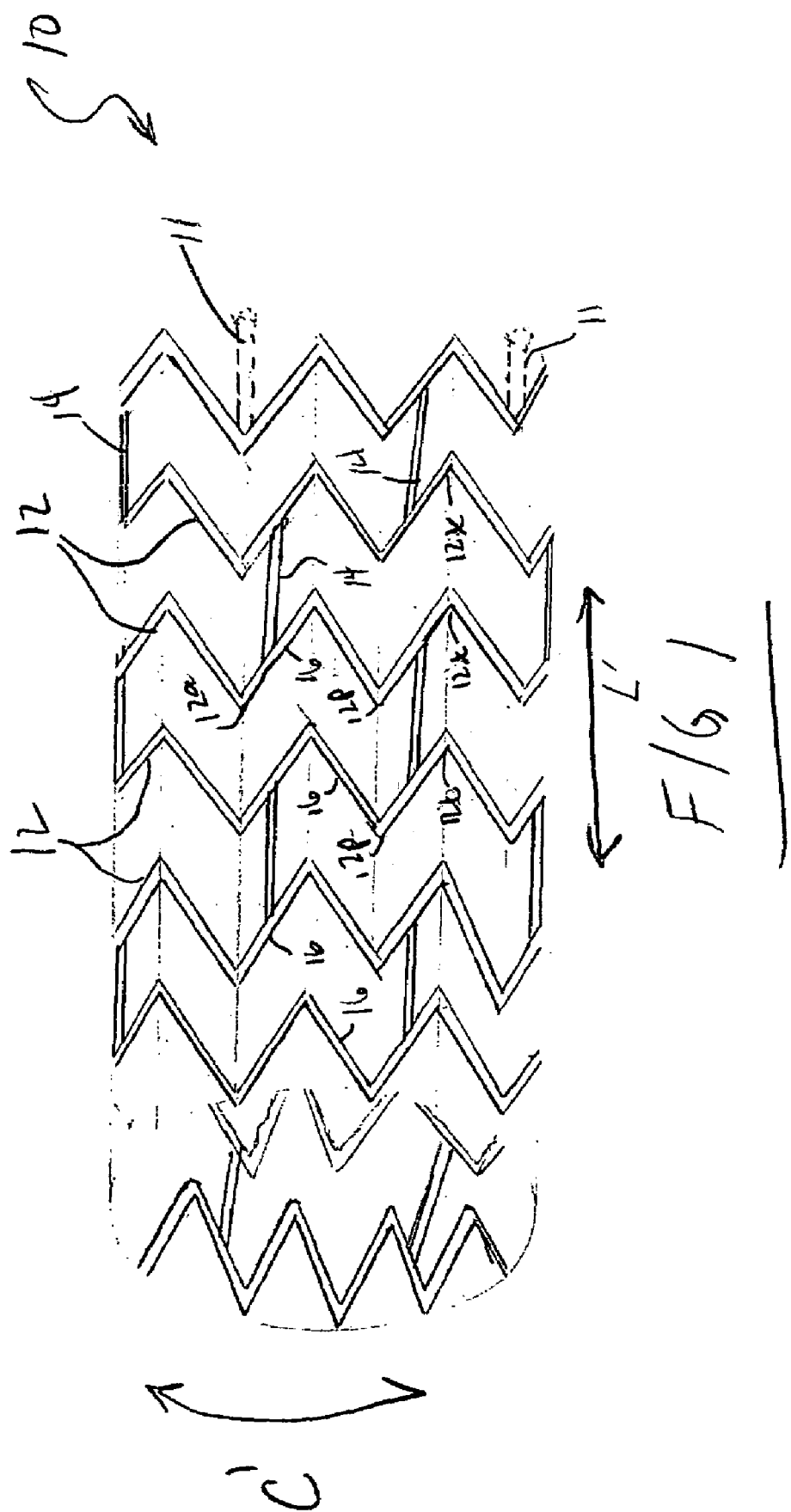
FIG. 1 is a perspective view of an endoluminal stent in its expanded diameter in accordance with the present invention.

In accordance with the present invention there is provided several preferred embodiments. In each of the preferred embodiments of the present invention, the general configuration of the inventive endoluminal stent is substantially the same. Specifically and with particular reference to FIG. 1, the inventive endoluminal stent 10 consists generally of a tubular cylindrical element comprised of a plurality of circumferential expansion elements 12 generally forming closed rings about the circumferential axis C' of the stent 10 and arrayed in spaced apart relationship relative to one another coaxially along the longitudinal axis L' of stent 10. A plurality of interconnecting members 14 interconnects adjacent pairs of the plurality of circumferential expansion elements 12. Each of the plurality of circumferential expansion elements 12 have a generally sinusoidal configuration with a plurality of peaks 12p and a plurality of troughs 12t of each circumferential expansion member and a plurality of struts 16 interconnecting adjacent peaks 12p and troughs 12t. The plurality of peaks 12p and the plurality of troughs 12t in one circumferential ring member 12 may either be in phase or out of phase with the plurality of peaks 12p and troughs 12t in adjacent circumferential ring members 12. Additionally, within each circumferential ring member 12, the peaks 12p and troughs 12t may have either regular or irregular periodicity or each of the plurality of circumferential expansion elements may have regions of regular periodicity and regions of irregular periodicity. Each of the plurality of interconnecting members 14 preferably comprise generally linear elements having a width $W_i$ that interconnect a strut 16 of a first circumferential expansion element 12 with a strut 16 of a second, adjacent circumferential element 12. Each of the plurality of interconnecting members has a generally rectangular transverse cross-sectional shape. In accordance with each preferred embodiment of the present invention, the interconnection between each of the plurality of interconnecting members 14 and the struts 16 occurs at an approximate mid-point along the length of the strut 16. Each of the plurality of struts 16 has a width $W_s$ and is generally rectangular in transverse cross-section.

Additionally, a plurality of terminal flange members 11, shown in phantom, may be provided in order to provide affixation points for mounting a graft covering (not shown) onto the stent 10. The terminal flange members 11 may be positioned at the distal end, the proximal end or both ends of the stent 10 and preferably are formed generally linear projections from either peak 12p or a trough 12t of a terminal circumferential expansion element 12 at either or both of the proximal or distal ends of the stent 10. Each of the plurality of flange members 11 may further include a rounded distal or proximal end region to facilitate affixation of a graft covering.

Figure 2:
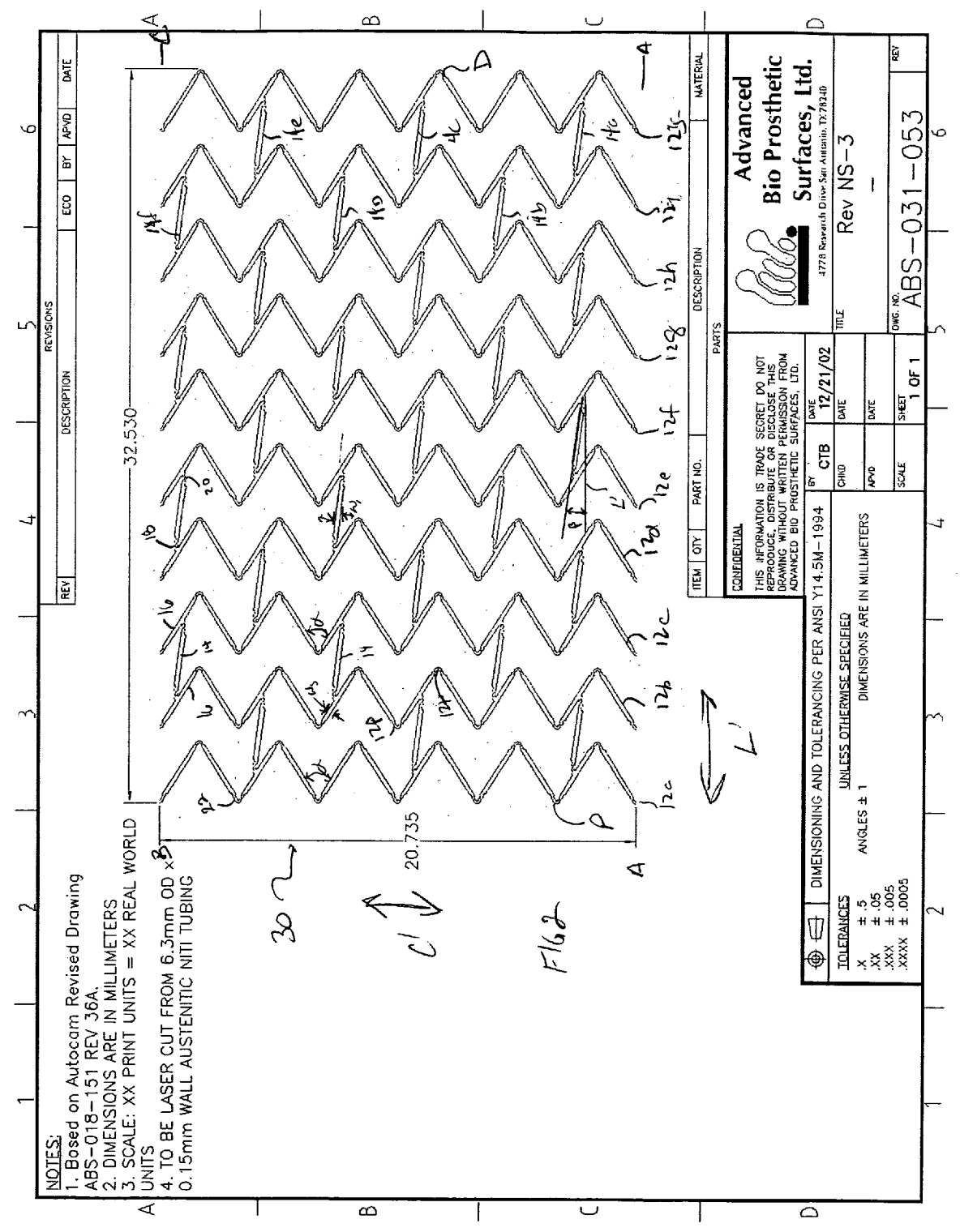
Figure 6:
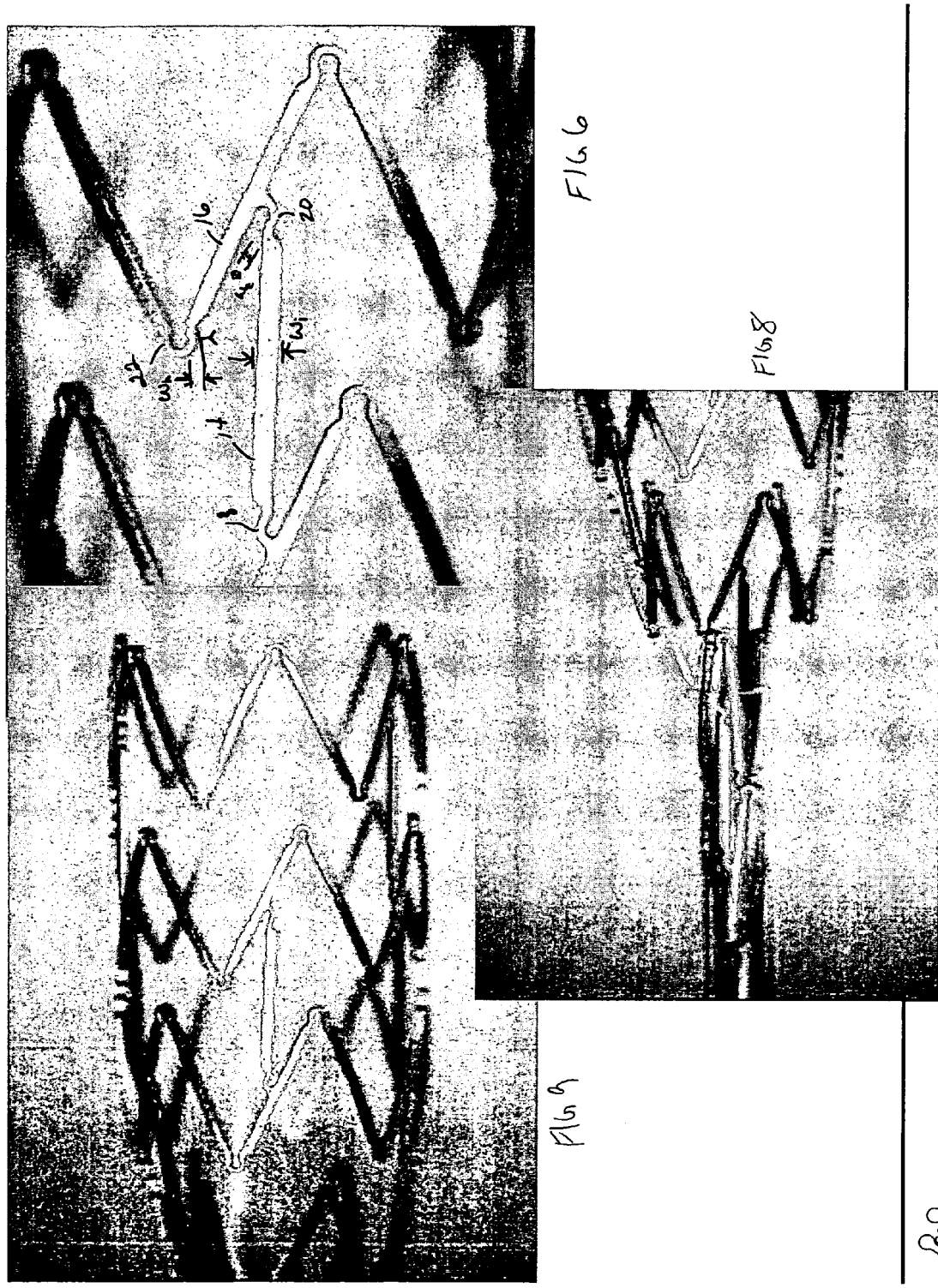
FIG. 6 is a photomicrograph of an interconnecting member and portions of circumferential expansion members of the inventive endoluminal stent.

With reference to FIGS. 2 and 6, to facilitate crimping the inventive stent 10 to its first, smaller delivery diameter, it has been found preferable to provide at each peak 12p and trough 12t a generally U-shaped hinge element 22 that connects adjacent struts along each circumferential expansion member 12. In accordance with the preferred embodiments of the invention, it is desirable that each generally U-shaped element hinge has a width $W_h$ that is less than $W_s$ of the struts 16 to which it is connected. By making $W_h$ less than $W_s$, it has been found that a greater degree of compression of the angle α formed between adjacent struts 16 interconnected by the generally U-shaped hinge element 22 may be achieved, thereby lending a greater degree of compressibility to the inventive stent 10 than that found where the U-shaped hinge element 22 was not employed.

Additionally, it has been found desirable, in accordance with the best mode for the present invention, to provide strain-relief sections 18 and 20 at opposing ends of each of the plurality of interconnecting members 14. The strain-relief sections 18 and 20 comprise terminal sections of the interconnecting member 14 and have a width $W_t$ that is less than the width $W_i$ of the interconnecting member 14. In accordance with one embodiment of the present invention, the strain-relief sections 18 and 20 each have a generally C-shaped configuration and traverse a radius in connecting the interconnection member 14 with the struts 16 of adjacent circumferential expansion members 12. Alternate geometric configurations of the C-shaped terminal strain-relief sections 18 and 20 are also contemplated by the present invention, such as S-shaped, V-shaped, M-shaped, W-shaped, U-shaped, or merely generally I-shaped extensions projecting co-axially along the longitudinal axis of each interconnecting member 14.

FIGS. 2–5 depict alternative preferred embodiments of the stent 10 of the present invention. Each of the preferred embodiments depicted in FIGS. 2–5 include the same circumferential expansion elements 12, each having a plurality of peaks 12p and troughs 12t and formed of a plurality of struts 16 interconnected at the peaks 12p and troughs 12t, and the generally U-shaped elements 22 forming the peaks 12p and troughs 12t, with adjacent pairs of circumferential expansion elements 12 being interconnected by the plurality of interconnecting members 14. Thus, in each of FIGS. 2–5, like elements are identified by like reference numerals. The alternative preferred embodiments of the inventive stent 30, 40, 50 and 60 illustrate in each of FIGS. 2, 3, 4 and 5, respectively, differ principally in the position and orientation of the plurality of interconnecting members 14. In FIGS. 2–5, each of the stents 30, 40, 50 and 60 are illustrated in planar views. Those skilled in the art will understand that the planar view is depicted for ease of illustration and that the stents depicted are tubular with lines A—A and B—B forming division lines along the longitudinal axis L' of the stents in order to illustrate the stent geometry in a planar view.

In FIG. 2, stent 30 is comprised of a plurality of circumferential expansion members 12 and a plurality of interconnecting members 14. Each of the plurality of interconnecting members 14 joins adjacent pairs of circumferential expansion members 12. Each interconnecting member 14 forms a junction with a strut 16 of each of the adjacent circumferential expansion members 12 and intersects the strut 16 at approximately a mid-point along the length of each strut 16. The plurality of interconnecting members 14 form groupings 14a, 14b, 14c, 14d, 14e and 14f along the longitudinal axis L' of the stent 30. Because the interconnecting members 14 lie in the folding planes of the peaks 12p and troughs 12t and struts 16 about angle α, it has been found desirable to offset each of the interconnecting members 14 from a line parallel to the longitudinal axis L' of the stent 30 by an angle β in order to enhance the folding properties of the circumferential expansion members 12 from a larger diameter to a smaller diameter of the stent 30. In stent 30, each of the plurality of interconnecting members 14 in groupings 14a–14f have the same offset angle β and all of the plurality of interconnecting members 14 are parallel to each other. In order to accommodate the offset angle β, and provide for folding of the interconnecting members 14 during compression of the stent 30 from its larger diameter to its smaller diameter, the strain relief sections 18 and 20 at terminal ends of each interconnecting member 14 have opposing orientations. Thus, when stent 30 is viewed in its tubular configuration from a proximal end view P, first strain relief section 18 has a generally C-shaped configuration that has a right-handed or clockwise orientation, while the second strain relief section 20, also having a generally C-shaped configuration has a generally left-handed or counterclockwise orientation.

In accordance with the preferred embodiment for stent 30, it has been found desirable to employ a 2:1 ratio of peaks 12p or troughs 12t to interconnecting members. Thus, as depicted, there are six peaks 12p and six troughs 12t in each of the plurality of circumferential expansion elements 12 and three interconnecting members 14 interconnect each pair of adjacent circumferential expansion elements 12. Similarly, between adjacent pairs of circumferential expansion elements 12, the interconnecting members 14 are circumferentially offset one peak 12p and one trough 12t from the interconnecting members 14 in an adjacent pair of circumferential expansion elements 12. Thus, interconnecting elements in groups 14a, 14c and 14e interconnect circumferential expansion element pairs 12a–12b, 12c–12d, 12e–12f, 12g–12h and 12i–12j, interconnecting elements in groups 14b, 14d and 14f interconnect circumferential expansion element pairs 12b–12c, 12d–12e, 12f–12g, 12h–12i. With the interconnecting elements in group 14a, 14c and 14e each being offset by one peak 12p and one trough 12t along the circumferential axis of each circumferential expansion element 12.

Figure 3:
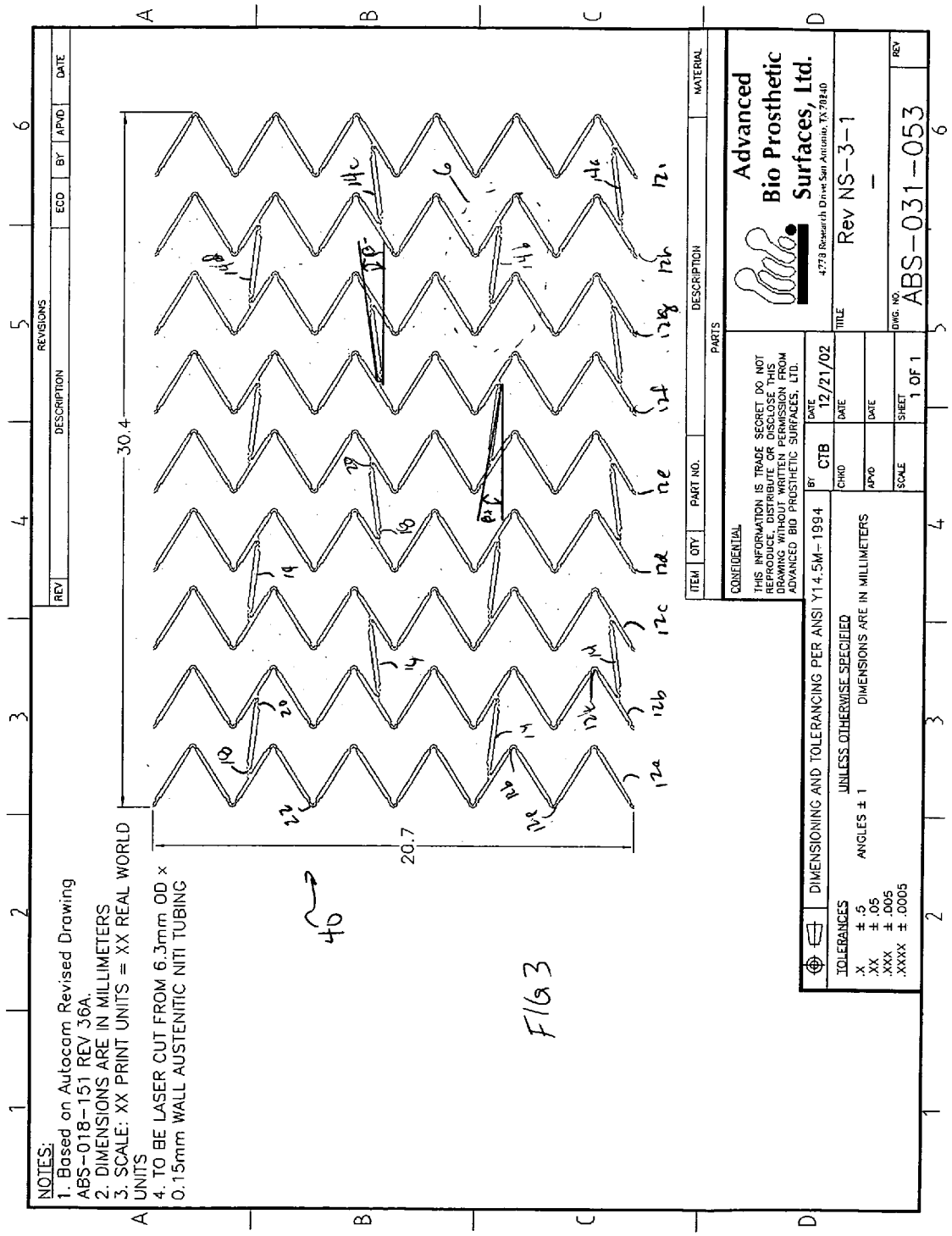
FIG. 3 is a plan view of a second embodiment of the inventive endoluminal stent.

Turning to FIG. 3, stent 40 is illustrated and has a substantially identical configuration of circumferential expansion elements 12 and interconnecting elements 14, except that instead of employing a 2:1 ratio of peaks 12p or troughs 12t to interconnecting elements, stent 40 employs a 3:1 ratio, such that each circumferential expansion element 12a–12i has six peaks 12p and six troughs 12t, but adjacent pairs of circumferential elements 12 are interconnected by only two interconnecting elements 14. Like stent 30, the interconnecting elements of a first circumferential expansion element pair are circumferentially offset from the interconnecting elements of a second adjacent circumferential expansion element pair, except in stent 40, the offset is either one peak 12p and two troughs 12t or two peaks 12p and one trough 12t. In stent 40 there are four groups of interconnecting elements 14a, 14b, 14c and 14d that interconnect the plurality of circumferential expansion elements 12. Interconnecting element groups 14a and 14c interconnects circumferential expansion element pairs 12b–12c, 12d–12e, 12f–12g and 12h–12i, and interconnecting element groups 14b and 14d interconnect circumferential expansion element pairs 12a–12b, 12c–12d, 12e–12f and 12g–12h.

In stent 40, each of the interconnecting elements 14 are also angularly offset from the longitudinal axis of the stent by an angle β, except that the plurality of interconnecting elements 14 are not all parallel relative to each other. Rather, the interconnecting elements in interconnecting element groups 14a and 14c are parallel to each other and the interconnecting elements in interconnecting elements groups 14b and 14d are parallel to each other, with the interconnecting elements in groups 14a and 14c being offset from the longitudinal axis of the stent by an angle β− which is alternate to the angle β, also denoted angle β+, forming the offset from the longitudinal axis L' for the interconnecting elements in groups 14b and 14d. The designation angle β+ and angle β− is intended to denote that these angles represent the substantially the same angular offset from the longitudinal axis L', but have alternate orientations relative to the circumferential axis of the stent 40.

Figure 4:
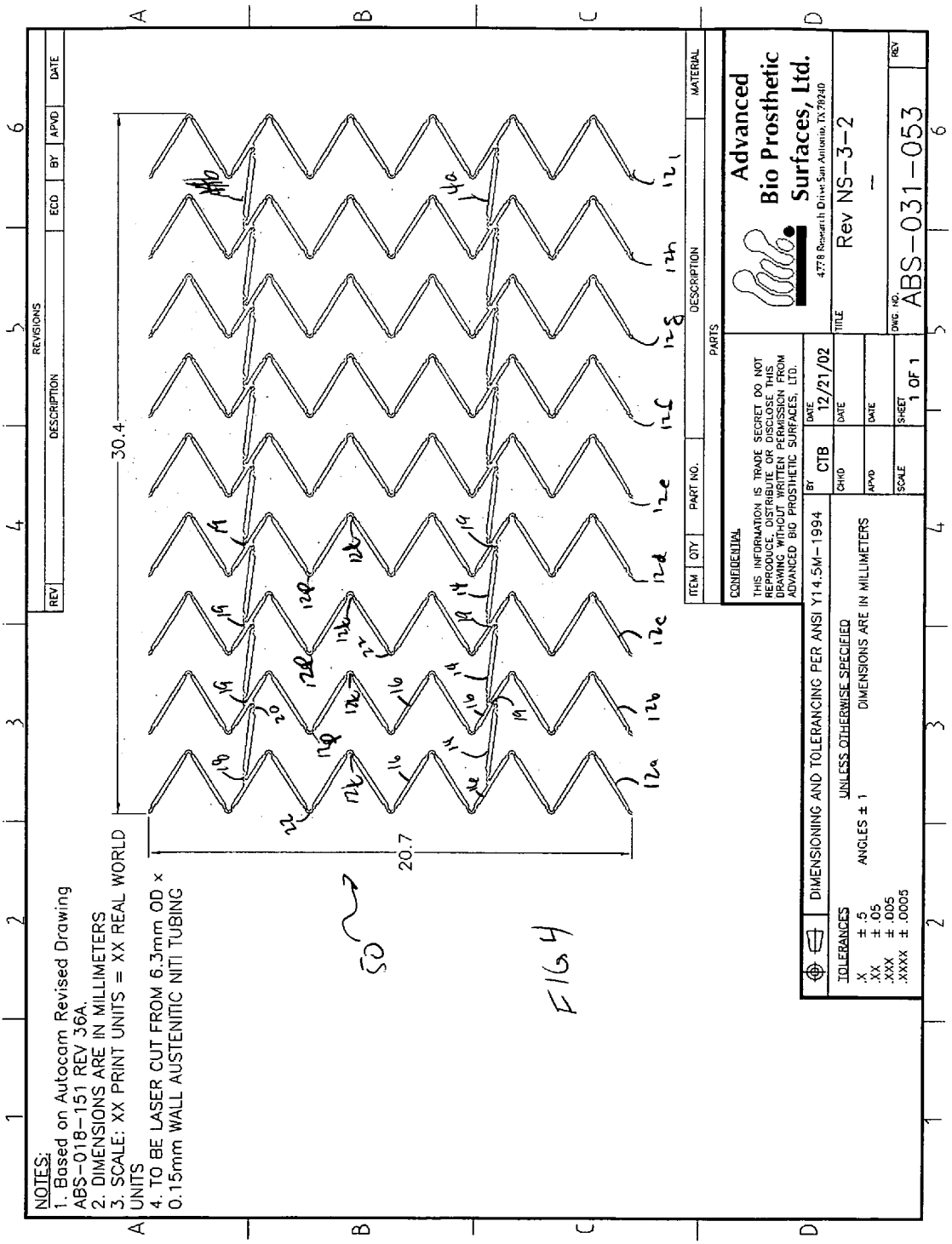
FIG. 4 is a plan view of a third embodiment of the inventive endoluminal stent.

Turning now to FIG. 4 in which stent 50 is depicted. Like stents 30 and 40 described above, stent 50 shares the common elements of circumferential expansion elements 12, having a plurality of peaks 12p and troughs 12t interconnecting a plurality of struts 16, and U-shaped sections 22, and interconnecting elements 14. In stent 50, however, the plurality of interconnecting elements 14 form two groups of interconnecting elements 14a and interconnecting elements 14b. Each of the individual interconnecting elements 14 in interconnecting element groups 14a and 14b are also angularly offset from the longitudinal axis L' of the stent 50 by angle β. Moreover, within each pair of adjacent circumferential expansion elements 12, the interconnecting element groups 14a and 14b are circumferentially offset from each other by three peaks 12p and three troughs 12t. Within each group of interconnecting elements 14a and 14b, however, each of the plurality of individual interconnecting elements 14 are generally aligned along a common longitudinal axis. In this manner, with the exception of the most proximal 12a and the most distal 12i circumferential ring elements, each of the plurality of interconnecting elements form a substantially four-point junction 19 at approximately a mid-point a strut 16 on each of circumferential expansion elements 12b–12h. The substantially four-point junction 19 is formed between a distal strain relief section 20 of one interconnecting member with a proximal side of a strut 16 and a proximal strain relief section 18 of an adjacent interconnecting element 14 with a distal side of the same strut 16.

Figure 5:
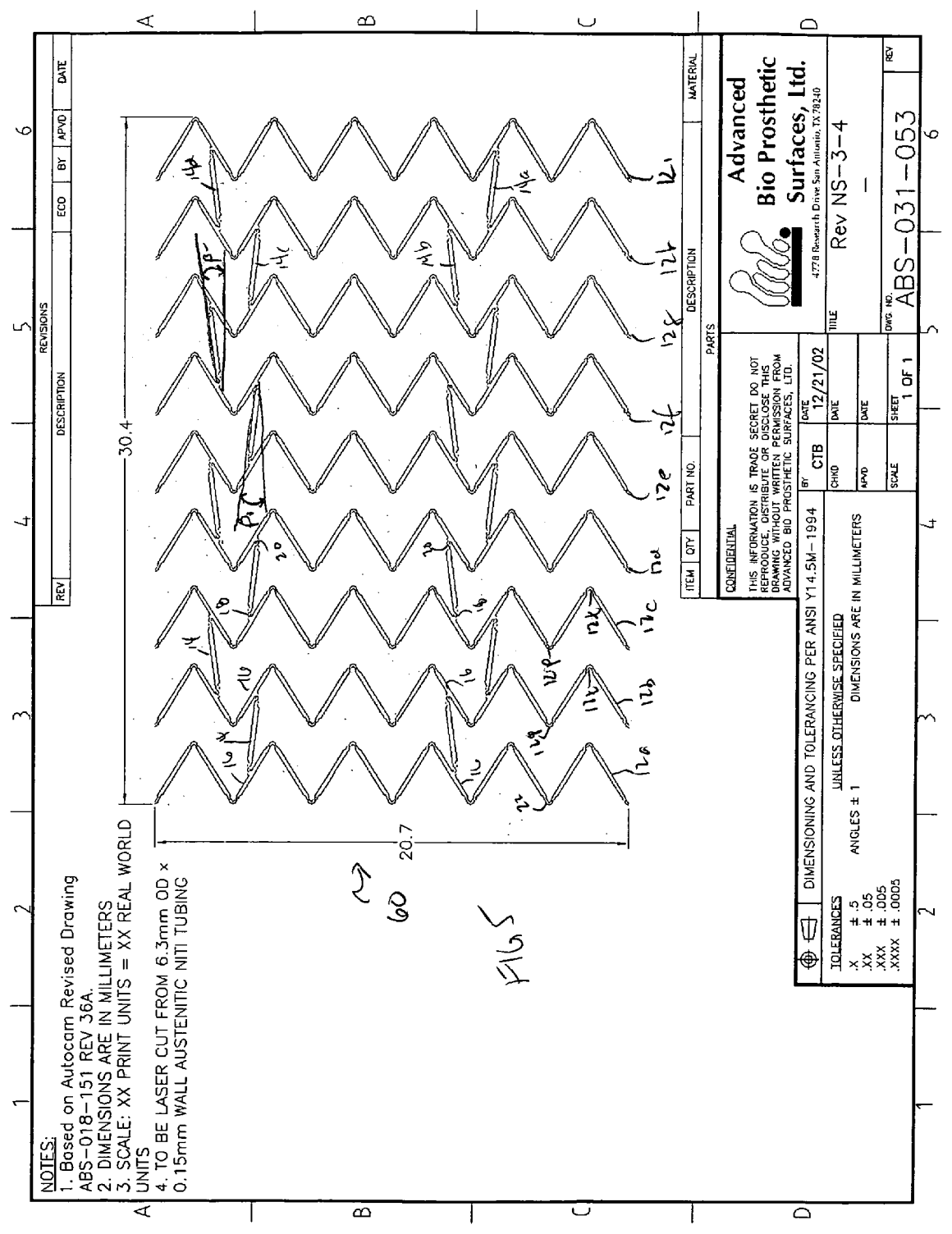

Finally, turning to FIG. 5, there is illustrated stent 60 which, like stents 30, 40 and 50 is comprised of a plurality of circumferential expansion elements 12 and interconnecting elements 14 that interconnect adjacent pairs of circumferential expansion elements 12. Like stent 40 of FIG. 3, stent 60 has groupings of interconnecting elements 14 into interconnecting element groups 14a, 14b, 14c and 14d. In stent 60, however, interconnecting element groups 14a and 14d interconnect identical pairs of circumferential expansion elements 12 and interconnecting element groups 14b and 14c interconnect identical pairs of circumferential expansion elements 12. Each of the interconnecting elements in interconnecting element groups 14b and 14d are angularly offset from the longitudinal axis L' of the stent 60 by an angle β− and are parallel to one and other. Similarly, each of the interconnecting elements in interconnecting element groups 14a and 14c are angularly offset from the longitudinal axis L' of the stent 60 by an angle β+ and are parallel to one and other.

For each adjacent pair of circumferential expansion elements 12, the interconnecting elements 14 have different orientations of angular offset from the longitudinal axis L' of the stent 50. For example, for circumferential expansion element pair 12a–12b, the interconnecting elements of group 14b and group 14c are offset by angle β− and by angle β+, respectively. In the adjacent circumferential expansion element pair 12b–12c, the interconnecting elements of group 14a and 14d are offset by angle β+ and by angle β−, respectively. Thus, between adjacent pairs of circumferential elements 12, the interconnecting elements are out of phase, in that they have different angular orientations of angle β. Additionally, between adjacent pairs of circumferential elements 12, the interconnecting elements are circumferentially offset by a single peak 12p, with interconnecting element group 14a being circumferentially offset from interconnecting element group by a single peak 12p, and interconnecting element group 14c being circumferentially offset from interconnecting element group 14d by a single peak 12p. Furthermore, there are different circumferential offsets between interconnecting element group pairs 14b–14c and 14a–14d within individual pairs of adjacent circumferential expansion elements 12. The circumferential offset between interconnecting element group pair 14b–14c is two peaks 12p and three troughs 12t, while the circumferential offset between interconnecting element group pair 14a–14d is four peaks 12p and three troughs 12t.

Those skilled in the art will appreciate that the foregoing embodiment of stents 10, 20, 30, 40 and 50 describe various geometries all comprised of common structural elements, namely, circumferential expansion elements 12 having a plurality of peaks 12p and troughs 12t and struts 16 interconnected by hinge elements 22. Furthermore, those skilled in the art will understand that variations on the number of and positioning of the interconnecting members 14 between adjacent pairs of circumferential expansion elements 12 and along the circumferential axis of the stent are also contemplated by the present invention and that the specific embodiments illustrated and described with reference to the figures is exemplary in nature.

FIG. 3, however, represents a particularly preferred embodiment of the inventive stent 40. Inventive stent 40 was fabricated by laser-cutting the described geometry from a nickel-titanium hypotube. After laser cutting, the stent 40 was annealed to set shape memory properties for the stent 40 with a fully expanded, enlarged outer diameter of 5.8 mm and a length of 30.6 mm. Stent 40 was capable of being crimped to a smaller, crimped outer diameter of 1.4 mm and was placed within a constraining sheath as illustrated in FIG. 7. Stent 40 exhibited excellent crimpability with the struts 16 folding at the generally U-shaped hinge elements 22 through angle α without appreciable interference between the circumferential expansion elements 12 and the interconnecting elements 14.

During radial expansion of the stent 40 from its first constrained smaller diameter, i.e., 1.4 mm, to its second enlarged radially expanded diameter, i.e., 5.8 mm, the stent 40 exhibited no foreshortening characteristic of many stent geometries known in the art. In contrast to foreshortening the stent 40 unexpectedly elongated by 2.5%. Heretofore a stent that elongates upon radial expansion is unknown in the art.

FIG. 8 depicts stent 40 radially expanding as it the constraining sheath is being withdrawn from the stent 40. FIG. 9 depicts stent 40 in virtually its fully radially expanded enlarged diameter, with just a proximal section of the stent 40 be constrained in the constraining sheath (not pictured). FIG. 6 is an enlarged section of the stent 40 illustrating the mid-strut connection between the circumferential expansion element 12 and the interconnecting element 14 at the proximal and distal strain relief sections 18 and 20, and clearly showing the generally U-shaped hinge elements 22, the peaks 12p and troughs 12t of each circumferential expansion element 12. FIG. 6 also clearly depicts the differences in the widths $W_t$ of the proximal and distal strain relief sections and the width $W_1$ of the body of the interconnecting member 14, as well as the difference between the width $W_h$ of the U-shaped hinge element 22 and the width $W_s$ of the strut 16.

The plurality of circumferential expansion elements 12 and interconnecting members 14, and components sections thereof, are preferably made of materials selected from the group consisting of titanium, vanadium, aluminum, nickel, tantalum, zirconium, chromium, silver, gold, silicon, magnesium, niobium, scandium, platinum, cobalt, palladium, manganese, molybdenum and alloys thereof, and nitinol and stainless steel. The plurality of circumferential expansion elements 12 and the plurality of interconnecting members 14 may be made of the same material or of different materials and have the same material properties or have different material properties. The term "material properties" is intended to encompass physical properties, including without limitation, elasticity, tensile strength, mechanical properties, hardness, bulk and/or surface grain size, grain composition, and grain boundary size, intra and inter-granular precipitates. Similarly, the materials selected for the plurality of circumferential expansion elements 12 and the plurality of interconnecting members 14 may be selected to have the same or different chemical properties. The term "chemical properties" is intended to encompass both any chemical reaction and change of state that the material may undergo after being implanted into a body and the physiological response of the body to the material after implantation.

While the inventive stents may be fabricated by chemical, thermal or mechanical ablative methods known in the art, such as chemical etching, laser cutting, EDM or water jet processes, it is envisioned that a preferred method for fabricating the inventive stents is by physical vapor deposition techniques. Physical vapor deposition techniques afford the ability to tightly control both the tolerances of the stent geometries as well as the physical and chemical properties of the stent and the stent materials. The inventive stents 10, 30, 40, 50 and 60, including each of their elements, namely the plurality of circumferential expansion elements 12 and interconnecting members 14 and component sections thereof, are preferably made of a bulk material having controlled heterogeneities on the luminal surface thereof. As is described in co-pending, commonly assigned, U.S. patent application Ser. No. 09/754,304 filed Dec. 22, 2000, which is a divisional of U.S. Pat. No. 6,379,383 issued Apr. 30, 2002, which is hereby incorporated by reference, heterogeneities are controlled by fabricating the bulk material of the stent to have defined grain sizes, chemical and intra- and intergranular precipitates and where the bulk and surface morphology differ, yielding areas or sites along the surface of the stent while maintaining acceptable or optimal protein binding capability. The characteristically desirable properties of the inventive stent are: (a) optimum mechanical properties consistent with or exceeding regulatory approval criteria, (b) minimization of defects, such as cracking or pin hole defects, (c) a fatigue life of 400 MM cycles as measured by simulated accelerated testing, (d) corrosion and/or corrosion-fatigue resistance, (e) biocompatibility without having biologically significant impurities in the material, (f) a substantially non-frictional abluminal surface to facilitate atraumatic vascular crossing and tracking and compatible with transcatheter techniques for stent introduction, (g) radiopaque at selected sites and MRI compatible, (h) have a luminal surface which is optimized for surface energy and microtopography, (i) minimal manufacturing and material cost consistent with achieving the desired material properties, and (j) high process yields.

In accordance with the present invention, the foregoing properties are achieved by fabricating a stent by the same metal deposition methodologies as are used and standard in the microelectronics and nano-fabrication vacuum coating arts, and which are hereby incorporated by reference. The preferred deposition methodologies include ion-beam assisted evaporative deposition and sputtering techniques. In ion beam-assisted evaporative deposition it is preferable to employ dual and simultaneous thermal electron beam evaporation with simultaneous ion bombardment of the substrate using an inert gas, such as argon, xenon, nitrogen or neon. Bombardment with an inert gas, such as argon ions serves to reduce void content by increasing the atomic packing density in the deposited material during deposition. The reduced void content in the deposited material allows the mechanical properties of that deposited material to be similar to the bulk material properties. Deposition rates up to 20 nm/sec are achievable using ion beam-assisted evaporative deposition techniques.

When sputtering techniques are employed, a 200-micron thick stainless steel film may be deposited within about four hours of deposition time. With the sputtering technique, it is preferable to employ a cylindrical sputtering target, a single circumferential source that concentrically surrounds the substrate that is held in a coaxial position within the source. Alternate deposition processes which may be employed to form the stent in accordance with the present invention are cathodic arc, laser ablation, and direct ion beam deposition. When employing vacuum deposition methodologies, the crystalline structure of the deposited film affects the mechanical properties of the deposited film. These mechanical properties of the deposited film may be modified by post-process treatment, such as by, for example, annealing, high-pressure treatment or gas quenching.

Materials to make the inventive stents are chosen for their biocompatibility, mechanical properties, i.e., tensile strength, yield strength, and their ease of deposition include the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

During deposition, the chamber pressure, the deposition pressure and the partial pressure of the process gases are controlled to optimize deposition of the desired species onto the substrate. As is known in the microelectronic fabrication, nano-fabrication and vacuum coating arts, both the reactive and non-reactive gases are controlled and the inert or non-reactive gaseous species introduced into the deposition chamber are typically argon and nitrogen. The substrate may be either stationary or moveable, either rotated about its longitudinal axis, or moved in an X-Y plane within the reactor to facilitate deposition or patterning of the deposited material onto the substrate. The deposited material may be deposited either as a uniform solid film onto the substrate, or patterned by (a) imparting either a positive or negative pattern onto the substrate, such as by etching or photolithography techniques applied to the substrate surface to create a positive or negative image of the desired pattern or (b) using a mask or set of masks which are either stationary or moveable relative to the substrate to define the pattern applied to the substrate. Patterning may be employed to achieve complex finished geometries of the resultant stent, both in the context of spatial orientation of the pattern as well as the material thickness at different regions of the deposited film, such as by varying the wall thickness of the material over its length to thicken sections at proximal and distal ends of the stent to prevent flaring of the stent ends upon radial expansion of the stent.

The stent may be removed from the substrate after stent formation by any of a variety of methods. For example, the substrate may be removed by chemical means, such as etching or dissolution, by ablation, by machining or by ultrasonic energy. Alternatively, a sacrificial layer of a material, such as carbon or aluminum, may be deposited intermediate the substrate and the stent and the sacrificial layer removed by melting, chemical means, ablation, machining or other suitable means to free the stent from the substrate.

The resulting stent may then be subjected to post-deposition processing to modify the crystalline structure, such as by annealing, or to modify the surface topography, such as by etching to affect and control the heterogeneities on the blood flow surface of the stent.

A plurality of microgrooves may be imparted onto the luminal and/or abluminal surface of the stent 10, as is more fully described in International Publication No. WO 99/23977, published 20 May 1999, which is commonly assigned with the present application and is hereby incorporated by reference. The plurality of microgrooves may be formed either as a post-deposition process step, such as by etching, or during deposition, such as by depositing the stent-forming material onto a mandrel which has a microtopography on the surface thereof which causes the metal to deposit with the microgroove pattern as part of the deposited material.

Each of the preferred embodiments of the present invention are preferably fabricated by employing a vapor deposition technique which entails vapor depositing a stent-forming metal onto a substrate. The substrate may be planar or cylindrical and is either pre-patterned with one of the preferred geometries of first and interconnecting members, in either positive or negative image, or the substrate may be un-patterned. Where the substrate is un-patterned, the deposited stent-forming metal is subjected to post-deposition patterning to pattern the deposited stent-forming metal into one of the preferred geometries of the first and interconnecting members. In all embodiments of the present invention fabricated by vapor deposition techniques, the need for post-deposition processing of the patterned endoluminal stent, e.g., modifying the surface of the stent by mechanical, electrical, thermal or chemical machining or polishing, is eliminated or minimized.

Vapor deposition fabrication of the inventive endoluminal stents offers many advantages, including, for example, the ability to fabricate stents of complex geometries, ultrafine dimensional tolerances on the order of Angstroms, the ability to control fatigue life, corrosion resistance, corrosion fatigue, inter- and intra-granular precipitates and their effect on corrosion resistance and corrosion fatigue, bulk material composition, bulk and surface material properties, radioopacity, and the ability to vary the transverse profiles, Z-axis thickness and X-Y-axis surface area of the stent structural elements in manners that affect the longitudinal flexibility, hoop strength, and radial expansion behavior and profile of the stent. Bulk material composition may be adjusted to employ elemental fractions in alloy compositions that are not feasible when using conventionally formed metals. This results in achieving the ability to tailor the alloy compositions in a manner that optimizes the alloy composition for a desired material or mechanical property. For example, nickel-titanium tubes exhibiting shape memory and/or superelastic properties were made employing in excess of 51.5 atomic percent nickel, which is not achievable using conventional working techniques due to high plateau stresses exhibited by the material. Specifically, the present inventors have fabricated nickel-titanium alloy tubes employing the method of the present invention that contain between 51.5 and 55 atomic percent nickel.

Vapor deposition of the inventive endoluminal stent, in accordance with a preferred embodiment of the present invention, significantly reduces or virtually eliminates inter- and intra-granular precipitates in the bulk material. It is common practice in the nickel-titanium endoluminal device industry to control transition temperatures and resulting mechanical properties by altering local granular nickel-titanium ratios by precipitation regimens. In the present invention, the need to control precipitates for mechanical properties is eliminated. Where nickel-titanium is employed as the stent-forming metal in the present invention, local nickel-titanium ratios will be the same or virtually identical to the nickel-titanium ratios in the bulk material, while still allowing for optimal morphology and eliminating the need for employing precipitation heat treatment. The resulting deposited stent-forming metal exhibits superior corrosion resistance, and hence, resistance to corrosion fatigue, when compared to conventional wrought nickel-titanium alloys.

The plurality of circumferential expansion elements 12 and the plurality of interconnecting members 14 may be conformationally configured during vapor deposition to impart a generally rectangular, ovular or elliptical transverse cross-sectional profile with either right angled edges or with chamfered or curved leading and trailing luminal and abluminal surface edges in the longitudinal axis of the stent in order to provide better blood flow surface profiles.

While the present inventions have been described with reference to their preferred embodiments, those of ordinary skill in the art will understand and appreciate that a multitude of variations on the foregoing embodiments are possible and within the skill of one of ordinary skill in the vapor deposition and stent fabrication arts, and that the above-described embodiments are illustrative only and are not limiting the scope of the present invention which is limited only by the claims appended hereto.

What is claimed is:

1. An endoluminal stent comprising:
   a. a plurality of circumferential expansion elements co-axially spaced to form a tubular configuration and each having an undulating pattern of peaks and valleys interconnected by struts, wherein the struts form linear sections and are interconnected at the peaks and valleys by hinge elements; and
   b. a plurality of linear interconnecting elements interconnecting adjacent pairs of circumferential expansion elements and joined at approximate mid-points of adjacent struts along a longitudinal axis of the endoluminal stent, the interconnecting elements having curvilinear first and second terminal sections, each section of the first and second terminal section having a narrower width than a width of the interconnecting elements.

2. The endoluminal stent according to claim 1, wherein each of the plurality of circumferential expansion elements further comprises a zig-zag configuration along a circumferential axis of the endoluminal stent wherein the struts are uniform in width throughout the entire section of the struts.

3. The endoluminal stent according to claim 1, wherein the curvilinear first and second terminal sections are positioned at opposing ends of each interconnecting element that join with the struts.

4. The endoluminal stent according to claim 3, wherein each of the plurality of circumferential expansion elements are integral and monolithic with each of the plurality of interconnecting elements.

5. The endoluminal stent according to claim 4, wherein the curvilinear first and second terminal sections of the plurality of linear interconnecting elements further comprise C-shaped sections.

6. The endoluminal stent according to claim 1, wherein the plurality of linear interconnecting elements are all parallel to each other.

7. The endoluminal stent according to claim 1, wherein the plurality of linear interconnecting elements are arrayed as at least two groups of interconnecting elements along a longitudinal axis of the endoluminal stent, a first of the at least two groups having a different angular orientation relative to the longitudinal axis of the endoluminal stent than a second of the at least two groups.

8. The endoluminal stent according to claim 1, wherein the endoluminal stent elongates along the longitudinal axis of the endoluminal stent as it expands from a smaller diameter to a larger diameter.

9. An endoluminal stent comprising:
   a. a plurality of circumferential expansion elements co-axially spaced to form a generally tubular configuration, each having a generally undulating pattern of peaks and valleys interconnected by struts forming a generally zig-zag configuration along a circumferential axis of the endoluminal stent wherein the struts form generally linear sections and are interconnected at the peaks and valleys by hinge elements having a width narrower than a width of the struts; and
   b. a plurality of generally linear interconnecting elements comprising generally curvilinear first and second terminal sections at opposing ends of each interconnecting element that join with the struts, each of the generally curvilinear first and second terminal sections of the plurality of generally linear interconnecting elements further comprising generally C-shaped sections having a width narrower than a width of the remainder of the interconnecting element, the plurality of generally linear interconnecting elements interconnecting adjacent pairs of circumferential expansion elements and joined at approximate mid-points of adjacent struts along a longitudinal axis of the endoluminal stent; and
   wherein each of the plurality of circumferential expansion elements are integral and monolithic with each of the plurality of interconnecting elements.

10. An endoluminal stent comprising:
   a. a plurality of circumferential expansion elements co-axially spaced to form a tubular configuration and each having an undulating pattern of peaks and valleys interconnected by struts; and
   b. a plurality of linear interconnecting elements interconnecting adjacent pairs of circumferential expansion elements and joined by strain relief sections at approximate mid-points of adjacent struts along a longitudinal axis of the endoluminal stent;
   c. wherein the strain relief sections have a width narrower than a width of the interconnecting elements.

* * * * *